United States Patent [19]

Zhang et al.

[11] Patent Number: 5,846,779
[45] Date of Patent: Dec. 8, 1998

[54] NUCLEIC ACIDS ENCODING MURINE UCP3 GENES

[75] Inventors: Ning Zhang; M. Catherine Amaral; Jin-Long Chen, all of South San Francisco, Calif.

[73] Assignee: Tularik Inc., South San Francisco, Calif.

[21] Appl. No.: 937,466

[22] Filed: Sep. 25, 1997

[51] Int. Cl.$^6$ .............................. C12P 21/02; C12N 1/00; C12N 15/12; C12N 15/63

[52] U.S. Cl. .................... 435/69.1; 435/243; 435/320.1; 435/325; 435/410; 536/23.1; 536/23.5

[58] Field of Search ................................. 536/23.1, 23.5; 435/320.1, 325, 420, 243, 69.1; 530/300, 324, 325, 326, 327, 328, 329, 330, 350

[56] References Cited

PUBLICATIONS

Marra et al. EST# AA062091. GenBank–est106 database [CD–ROM]. Accessed Jun. 12, 1998, Sep. 23, 1996.

*Primary Examiner*—Terry A. McKelvey
*Attorney, Agent, or Firm*—Richard Aron Osman

[57] ABSTRACT

The invention provides methods and compositions relating to a novel family of genes, mUCP3s, involved in metabolic regulation. The polypeptides may be produced recombinantly from transformed host cells from the disclosed mUCP3 encoding nucleic acids or purified from mammalian cells. The invention provides isolated mUCP3 hybridization probes, knock-out/in constructs and primers capable of specifically hybridizing with the disclosed mUCP3 genes, mUCP3-specific binding agents such as specific antibodies, animals and cells modified with the subject mUCP3 nucleic acids, and methods of making and using the subject compositions in the biopharmaceutical industry.

20 Claims, 6 Drawing Sheets

MVGLQPSEVPPTTVKFLGAGTAACFADLLTFPLDTAKVRLQIQGENPGA 50

QSVQYRGVLGTILTMVRTEGPRSPYSGLVAGLHRQMSFASIRIGLYDSVK 100

QFYTPKGADHSSVAIRILAGCTTGAMAVTCAQPTDVVKVRFQAMIRLGTG 150

GERKYRGTMDAYRTIAREEGVRGLWKGTWPNITRNAIVNCAEMVTYDIIK 200

EKLLESHLFTDNFPCHFVSAFGAGFCATVVASPVDVVKTRYMNAPLGRYR 250

SPLHCMLKMAAQEGPTAFYKGFVPSFLRLGAWNVMMFVTYEQLKRALMKV 300

QVLRESPF 308

Fig 1

```
GTCAGCTGGT GCACAGGGCC AGTGCCGAGC CAGGGACAGC AGAGACAACA GTGAATGGTG    60
AGCCCGGCC  GTCAGATCCT GCTGCTACCT AATGGAGTGG AGCCTTAGGG TGCCCCTGCA   120
CTACCCAACC TTGGCTAGAC GCACAGCTTC CTCCCTGAAC TGAAGCAAAA GATTGCCAGG   180
CAAGCTCTCT CCTCGGACCT CCATAGGCAG CAAAGGAACC AGGCCCATTC CCCGGGACCA   240
TGGTTGGACT TCAGCCCTCC GAAGTGCCTC CCACAACGGT TGTGAAGTTC CTGGGGGCCG   300
GCACTGCGGC CTGTTTTGCG GACCTCCTCA CTTTTCCCCT GGACACCGCC AAGGTCCGTC   360
TGCAGATCCA AGGGGAGAAC CCAGGGGCTC AGAGCGTGCA GTACCGCGGT GTGCTGGGTA   420
CCATCCTGAC TATGGTGCGC ACAGAGGGTC CCCGCAGCCC CTACAGCGGA CTGGTCGCTG   480
GCCTGCACCG CCAGATGAGT TTTGCCTCCA TTCGAATTGG CCTCTACGAC TCTGTCAAGC   540
AGTTCTACAC CCCCAAGGGA GCGGACCACT CCAGCGTCGC CCAGCCCCAC TCTGGCAGGCT  600
GCACGACAGG AGCCATGGCA GTGACCTGCG CCCAGCCCAC GGATGTGGTG AAGGTCCGAT   660
TTCAAGCCAT GATACGCCTG GGAACTGGAG GAGAGAGGAA ATACAGAGGG ACTATGGATG   720
CCTACAGAAC CATCGCCCAGG GAGGAAGGAG TCAGGGGCCT GTGGAAAGGG ACTTGGCCCA   780
```

Fig 2a

| | | | | |
|---|---|---|---|---|
| ACATCACAAG | AAATGCCATT | GTCAACTGTG | CTGAGATGGT | GACCTACGAC | ATCATCAAGG | 840
| AGAAGTTGCT | GGAGTCTCAC | CTGTTTACTG | ACAACTTCCC | CTGTCACTTT | GTCTCTGCCT | 900
| TTGGAGCTGG | CTTCTGTGCC | ACAGTGGTGG | CCTCCCCCGT | GGATGTGGTA | AAGACCCGAT | 960
| ACATGAACGC | TCCCCTAGGC | AGGTACCGCA | GCCCTCTGCA | CTGTATGCTG | AAGATGGCGG | 1020
| CTCAGGAGGG | ACCCACGGCC | TTCTACAAAG | GATTTGTGCC | CTCCTTTCTG | CGTCTGGGAG | 1080
| CTTGGAACGT | GATGATGTTT | GTAACATATG | AGCAACTGAA | GAGGGCCTTA | ATGAAAGTCC | 1140
| AGTACTGCCG | GGAATCTCCG | TTTTGAACAA | GGCAAGCAGG | CTGCCTGAAA | CAGAACAAAG | 1200
| CGTCTCTGCC | CTGGGGACAC | AGGCCCACAC | GGTCCAAAAC | CCTGCACTGC | TGCTGACACG | 1260
| AGAAACTGAA | CTAAAAGAGG | AGAGTTTTAG | TCCTCCGTGT | TTCGTCCTAA | AACACCTCTG | 1320
| TTTTGCACTG | ACCTGATGGG | AAATAAATTA | TATTAATTTT | TAAACCCCTT | CCGGTTGGAT | 1380
| GCCTAATATT | TAGGCAAGAG | ACAACAAAGA | AAACCAGAGT | CAACTCCCTT | GAAATGTAGG | 1440
| AATAAAGGAT | GCATAATAAA | CAGGAAAGGC | ACAGGTTTTG | AGAAGATCAG | CCCACAGTGT | 1500
| TGTCCTTGAA | TCAAACAAAA | TGGTCGGAGG | AACCCTTCGG | CTTCAGCACA | AAGAGGTGAC | 1560

Fig 2b

```
TACAGCCTTC TGGTCACCAG ATGACTCCGC CCCTCTGTAA TGAGTCTGCC AAGTAGACTC   1620
TATCAAGATT CTGGGGAAAG GAGAAAGAAC ACATTGATAC TGCACAAATG AGTGGTGCTG   1680
GGCCCACCGA GGACACTGGA GGATGGAGCG TGATCTGGGA TAACAGTCCT TCTCTGTCTG   1740
CCTCATCAGG GTGTTGGGAA GATAGAAAGC GAAGCAGACA TGGAAGCACT TCCTAACAAG   1800
GCCTGTCATC GTCATCATCT ACAAATGTAA GCCTGAGGAC AATGTTTTAG GAGAGATTCT   1860
GTCCAGAGAA GTAGTTTGAG GAAAATGCAG TTTGTAGTGG TAAAGCCATG CACACCTGGA   1920
CTGCATGGTA AGGACCAGGG GTGACGGAAG CCATGGGGAT CCGGTGCCTG GTAACATCAA   1980
AGGGCTGTGG GGGGGGGGGG GCACTGCCTG TCCATCAGTT CAAAGCAGCA GGACTCAGAA   2040
TCTCCACCTT AGGGCAAGAA CGAGAACAGC TGCTCTTCTG CCTTCTCTCT CGGAGGTTTT   2100
CTCATCTCAG GGTCCTACCT GCCAGGCTCC TGACCAGCTC CACCTGCCCA CACTTCCTCC   2160
TGCTCTCGCT GCCTTTGGCT GCAGAGCCTT TGCTCCTCCT GTTAAGCCTT CAGTCTTCCA   2220
TCTGCAAAAG GGAGGGCAAA GCACAGGACC AACTTCCAAG CTTAAAAATG CACATCTGAC   2280
AACAAAATGG CTCAGTGGGG TCCATTCATG GGACCCACAT GGTGGAAGGA CAGAATGGAC   2340
```

Fig 2c

```
TCTTGCAAAT TGTCCTCTGA CCTCCATTTG AGCGCCCTAT ACATGTGACT GTACATATGT   2400
ACAAACACGA TAAAGATGGA AACACATGTA AAAACATAAA AATAAAAAGT TGTACTGGAT   2460
GTGGTGGTTT GAATGAGATG TTCCTCGTGT CTCGGGCATT TGAAGACTTG CTCCCCAGTT   2520
GTTGGGCGGCT GTTTGGGGAG GCTTAGAAGA TGTGGCCTTT TGGGAAGCAG GGTGTCATTG   2580
AGGACTGGCT TGGAGAGCCT AAAGATCCGA GGCACTCCCA GTTTCTCTGG TTTTTCATTT   2640
TGAGGTGTGA GGTCTTATTG GCTGCACCAG TCTCCATGCC TGTCTGTTGC CCGGCCTCCT   2700
CACCATGATG GACTTTTATC TCTCTGTACT TGTAAGCCCC AAATAAACCT TCCATCTGTG   2760
AAAAAAAAAA AAAAAAAAAA AA                                            2782
```

Fig 2d

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 2782 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
GTCAGCTGGT    GCACAGGGCC    AGTGCCGAGC    CAGGGACAGC    AGAGACAACA    GTGAATGGTG         60

AGGCCCGGCC    GTCAGATCCT    GCTGCTACCT    AATGGAGTGG    AGCCTTAGGG    TGGCCCTGCA        120

CTACCCAACC    TTGGCTAGAC    GCACAGCTTC    CTCCCTGAAC    TGAAGCAAAA    GATTGCCAGG        180

CAAGCTCTCT    CCTCGGACCT    CCATAGGCAG    CAAAGGAACC    AGGCCCATTC    CCCGGGACCA        240
```

| | | | | | |
|---|---|---|---|---|---|
|TGGTTGGACT|TCAGCCCTCC|GAAGTGCCTC|CCACAACGGT|TGTGAAGTTC|CTGGGGGCCG 300|
|GCACTGCGGC|CTGTTTTGCG|GACCTCCTCA|CTTTTCCCCT|GGACACCGCC|AAGGTCCGTC 360|
|TGCAGATCCA|AGGGGAGAAC|CCAGGGGCTC|AGAGCGTGCA|GTACCGCGGT|GTGCTGGGTA 420|
|CCATCCTGAC|TATGGTGCGC|ACAGAGGGTC|CCCGCAGCCC|CTACAGCGGA|CTGGTCGCTG 480|
|GCCTGCACCG|CCAGATGAGT|TTTGCCTCCA|TTCGAATTGG|CCTCTACGAC|TCTGTCAAGC 540|
|AGTTCTACAC|CCCCAAGGGA|GCGGACCACT|CCAGCGTCGC|CATCAGGATT|CTGGCAGGCT 600|
|GCACGACAGG|AGCCATGGCA|GTGACCTGCG|CCCAGCCCAC|GGATGTGGTG|AAGGTCCGAT 660|
|TTCAAGCCAT|GATACGCCTG|GGAACTGGAG|GAGAGAGGAA|ATACAGAGGG|ACTATGGATG 720|
|CCTACAGAAC|CATCGCCAGG|GAGGAAGGAG|TCAGGGGCCT|GTGGAAAGGG|ACTTGGCCCA 780|
|ACATCACAAG|AAATGCCATT|GTCAACTGTG|CTGAGATGGT|GACCTACGAC|ATCATCAAGG 840|
|AGAAGTTGCT|GGAGTCTCAC|CTGTTTACTG|ACAACTTCCC|CTGTCACTTT|GTCTCTGCCT 900|
|TTGGAGCTGG|CTTCTGTGCC|ACAGTGGTGG|CCTCCCCGGT|GGATGTGGTA|AAGACCCGAT 960|
|ACATGAACGC|TCCCCTAGGC|AGGTACCGCA|GCCCTCTGCA|CTGTATGCTG|AAGATGGCGG 1020|
|CTCAGGAGGG|ACCCACGGCC|TTCTACAAAG|GATTTGTGCC|CTCCTTTCTG|CGTCTGGGAG 1080|
|CTTGGAACGT|GATGATGTTT|GTAACATATG|AGCAACTGAA|GAGGGCCTTA|ATGAAAGTCC 1140|
|AGGTACTGCG|GGAATCTCCG|TTTTGAACAA|GGCAAGCAGG|CTGCCTGAAA|CAGAACAAAG 1200|
|CGTCTCTGCC|CTGGGGACAC|AGGCCCACAC|GGTCCAAAAC|CCTGCACTGC|TGCTGACACG 1260|
|AGAAACTGAA|CTAAAAGAGG|AGAGTTTTAG|TCCTCCGTGT|TTCGTCCTAA|AACACCTCTG 1320|
|TTTTGCACTG|ACCTGATGGG|AAATAAATTA|TATTAATTTT|TAAACCCCTT|CCGGTTGGAT 1380|
|GCCTAATATT|TAGGCAAGAG|ACAACAAAGA|AAACCAGAGT|CAACTCCCTT|GAAATGTAGG 1440|
|AATAAAGGAT|GCATAATAAA|CAGGAAAGGC|ACAGGTTTTG|AGAAGATCAG|CCCACAGTGT 1500|
|TGTCCTTGAA|TCAAACAAAA|TGGTCGGAGG|AACCCTTCGG|CTTCAGCACA|AAGAGGTGAC 1560|
|TACAGCCTTC|TGGTCACCAG|ATGACTCCGC|CCCTCTGTAA|TGAGTCTGCC|AAGTAGACTC 1620|
|TATCAAGATT|CTGGGGAAAG|GAGAAAGAAC|ACATTGATAC|TGCACAAATG|AGTGGTGCTG 1680|
|GGCCCACCGA|GGACACTGGA|GGATGGAGCG|TGATCTGGGA|TAACAGTCCT|TCTCTGTCTG 1740|
|CCTCATCAGG|GTGTTGGGAA|GATAGAAAGC|GAAGCAGACA|TGGAAGCACT|TCCTAACAAG 1800|
|GCCTGTCATC|GTCATCATCT|ACAAATGTAA|GCCTGAGGAC|AATGTTTTAG|GAGAGATTCT 1860|
|GTCCAGAGAA|GTAGTTTGAG|GAAAATGCAG|TTTGTAGTGG|TAAAGCCATG|CACACCTGGA 1920|
|CTGCATGGTA|AGGACCAGGG|GTGACGGAAG|CCATGGGGAT|CCGGTGCCTG|GTAACATCAA 1980|
|AGGGCTGTGG|GGGGGGGGG|GCACTGCCTG|TCCATCAGTT|CAAAGCAGCA|GGACTCAGAA 2040|
|TCTCCACCTT|AGGGCAAGAA|CGAGAACAGC|TGCTCTTCTG|CCTTCTCTCT|CGGAGGTTTT 2100|
|CTCATCTCAG|GGTCCTACCT|GCCAGGCTCC|TGACCAGCTC|CACCTGCCCA|CACTTCCTCC 2160|
|TGCTCTCGCT|GCCTTTGGCT|GCAGAGCCTT|TGCTCCTCCT|GTTAAGCCTT|CAGTCTTCCA 2220|
|TCTGCAAAAG|GGAGGGCAAA|GCACAGGACC|AACTTCCAAG|CTTAAAAATG|CACATCTGAC 2280|
|AACAAAATGG|CTCAGTGGGG|TCCATTCATG|GGACCCACAT|GGTGGAAGGA|CAGAATGGAC 2340|
|TCTTGCAAAT|TGTCCTCTGA|CCTCCATTTG|AGCGCCCTAT|ACATGTGACT|GTACATATGT 2400|
|ACAAACACGA|TAAAGATGGA|AACACATGTA|AAAACATAAA|AATAAAAGT|TGTACTGGAT 2460|
|GTGGTGGTTT|GAATGAGATG|TTCCTCGTGT|CTCGGGCATT|TGAAGACTTG|CTCCCCAGTT 2520|
|GTTGGCGGCT|GTTTGGGGAG|GCTTAGAAGA|TGTGGCCTTT|TGGAAGCAG|GGTGTCATTG 2580|
|AGGACTGGCT|TGGAGAGCCT|AAAGATCCGA|GGCACTCCCA|GTTTCTCTGG|TTTTTCATTT 2640|

```
TGAGGTGTGA GGTCTTATTG GCTGCACCAG TCTCCATGCC TGTCTGTTGC CCGGCCTCCT      2700

CACCATGATG GACTTTTATC TCTCTGTACT TGTAAGCCCC AAATAAACCT TCCATCTGTG      2760

AAAAAAAAAA AAAAAAAAAA AA                                               2782
```

( 2 ) INFORMATION FOR SEQ ID NO:2:

( i ) SEQUENCE CHARACTERISTICS:
        ( A ) LENGTH: 308 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Met   Val   Gly   Leu   Gln   Pro   Ser   Glu   Val   Pro   Thr   Thr   Val   Val   Lys
 1                  5                        10                              15

Phe   Leu   Gly   Ala   Gly   Thr   Ala   Ala   Cys   Phe   Ala   Asp   Leu   Leu   Thr   Phe
                  20                        25                              30

Pro   Leu   Asp   Thr   Ala   Lys   Val   Arg   Leu   Gln   Ile   Gln   Gly   Glu   Asn   Pro
             35                              40                        45

Gly   Ala   Gln   Ser   Val   Gln   Tyr   Arg   Gly   Val   Leu   Gly   Thr   Ile   Leu   Thr
       50                              55                        60

Met   Val   Arg   Thr   Glu   Gly   Pro   Arg   Ser   Pro   Tyr   Ser   Gly   Leu   Val   Ala
 65                        70                              75                        80

Gly   Leu   His   Arg   Gln   Met   Ser   Phe   Ala   Ser   Ile   Arg   Ile   Gly   Leu   Tyr
                        85                              90                        95

Asp   Ser   Val   Lys   Gln   Phe   Tyr   Thr   Pro   Lys   Gly   Ala   Asp   His   Ser   Ser
                  100                       105                       110

Val   Ala   Ile   Arg   Ile   Leu   Ala   Gly   Cys   Thr   Thr   Gly   Ala   Met   Ala   Val
                  115                       120                       125

Thr   Cys   Ala   Gln   Pro   Thr   Asp   Val   Val   Lys   Val   Arg   Phe   Gln   Ala   Met
             130                             135                       140

Ile   Arg   Leu   Gly   Thr   Gly   Gly   Glu   Arg   Lys   Tyr   Arg   Gly   Thr   Met   Asp
145                             150                             155                       160

Ala   Tyr   Arg   Thr   Ile   Ala   Arg   Glu   Glu   Gly   Val   Arg   Gly   Leu   Trp   Lys
                        165                             170                       175

Gly   Thr   Trp   Pro   Asn   Ile   Thr   Arg   Asn   Ala   Ile   Val   Asn   Cys   Ala   Glu
                  180                             185                       190

Met   Val   Thr   Tyr   Asp   Ile   Ile   Lys   Glu   Lys   Leu   Leu   Glu   Ser   His   Leu
                  195                             200                       205

Phe   Thr   Asp   Asn   Phe   Pro   Cys   His   Phe   Val   Ser   Ala   Phe   Gly   Ala   Gly
       210                             215                       220

Phe   Cys   Ala   Thr   Val   Val   Ala   Ser   Pro   Val   Asp   Val   Val   Lys   Thr   Arg
225                             230                             235                       240

Tyr   Met   Asn   Ala   Pro   Leu   Gly   Arg   Tyr   Arg   Ser   Pro   Leu   His   Cys   Met
                        245                             250                       255

Leu   Lys   Met   Ala   Ala   Gln   Glu   Gly   Pro   Thr   Ala   Phe   Tyr   Lys   Gly   Phe
                  260                             265                       270

Val   Pro   Ser   Phe   Leu   Arg   Leu   Gly   Ala   Trp   Asn   Val   Met   Met   Phe   Val
             275                             280                       285

Thr   Tyr   Glu   Gln   Leu   Lys   Arg   Ala   Leu   Met   Lys   Val   Gln   Val   Leu   Arg
             290                             295                       300

Glu   Ser   Pro   Phe
305
```

( 2 ) INFORMATION FOR SEQ ID NO:3:

( i ) SEQUENCE CHARACTERISTICS:
( A ) LENGTH: 1949 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:3:

```
GTCAGCTGGT  GCACAGGGCC  AGTGCCGAGC  CAGGGACAGC  AGAGACAACA  GTGAATGGTG    60
AGGCCCGGCC  GTCAGATCCT  GCTGCTACCT  AATGGAGTGG  AGCCTTAGGG  TGGCCCTGCA   120
CTACCCAACC  TTGGCTAGAC  GCACAGCTTC  CTCCCTGAAC  TGAAGCAAAA  GATTGCCAGG   180
CAAGCTCTCT  CCTCGGACCT  CCATAGGCAG  CAAAGGAACC  AGGCCCATTC  CCCGGGACCA   240
TGGTTGGACT  TCAGCCCTCC  GAAGTGCCTC  CCACAACGGT  TGTGAAGTTC  CTGGGGGCCG   300
GCACTGCGGC  CTGTTTTGCG  GACCTCCTCA  CTTTTCCCCT  GGACACCGCC  AAGGTCCGTC   360
TGCAGATCCA  AGGGGAGAAC  CCAGGGGCTC  AGAGCGTGCA  GTACCGCGGT  GTGCTGGGTA   420
CCATCCTGAC  TATGGTGCGC  ACAGAGGGTC  CCCGCAGCCC  CTACAGCGGA  CTGGTCGCTG   480
GCCTGCACCG  CCAGATGAGT  TTTGCCTCCA  TTCGAATTGG  CCTCTACGAC  TCTGTCAAGC   540
AGTTCTACAC  CCCCAAGGGA  GCGGACCACT  CCAGCGTCGC  CATCAGGATT  CTGGCAGGCT   600
GCACGACAGG  AGCCATGGCA  GTGACCTGCG  CCCAGCCCAC  GGATGTGGTG  AAGGTCCGAT   660
TTCAAGCCAT  GATACGCCTG  GGAACTGGAG  GAGAGAGGAA  ATACAGAGGG  ACTATGGATG   720
CCTACAGAAC  CATCGCCAGG  GAGGAAGGAG  TCAGGGGCCT  GTGGAAAGGG  ACTTGGCCCA   780
ACATCACAAG  AAATGCCATT  GTCAACTGTG  CTGAGATGGT  GACCTACGAC  ATCATCAAGG   840
AGAAGTTGCT  GGAGTCTCAC  CTGTTTACTG  ACAACTTCCC  CTGTCACTTT  GTCTCTGCCT   900
TTGGAGCTGG  CTTCTGTGCC  ACAGTGGTGG  CCTCCCCGGT  GGATGTGGTA  AAGACCCGAT   960
ACATGAACGC  TCCCCTAGGC  AGGTACCGCA  GCCCTCTGCA  CTGTATGCTG  AAGATGGTGG  1020
CTCAGGAGGG  ACCCACGGCC  TTCTACAAAG  GATTTGTGCC  CTCCTTTCTG  CGTCTGGGAG  1080
CTTGGAACGT  GATGATGTTT  GTAACATATG  AGCAACTGAA  GAGGGCCTTA  ATGAAAGTCC  1140
AGGGTGTTGG  GAAGATAGAA  AGCGAAGCAG  ACATGGAAGC  ACTTCCTAAC  AAGGCCTGTC  1200
ATCGTCATCA  TCTACAAATG  GCAAGAACGA  GAACAGCTGC  TCTTCTGCCC  TCTCTCTCGG  1260
AGGTTTTCTC  ATCTCAGGGT  CCTACCTGCC  AGGCTCCTGA  CCAGCTCCAC  CTGCCCACAC  1320
TTCCTCCTGC  TCTCGCTGCC  TTTGGCTGCA  GAGCCTTTGC  TCCTCCTGTT  AAGCCTTCAG  1380
TCTTCCATCT  GCAAAAGGGA  GGGCAAAGCA  CAGGACCAAC  TTCCAAGCTT  AAAAATGCAC  1440
ATCTGACAAC  AAAATGGCTC  AGTGGGGTCC  ATTCATGGGA  CCCACATGGT  GGAAGGACAG  1500
AATGGACTCT  TGCAAATTGT  CCTCTGACCT  CCATTTGAGC  GCCCTATACA  TGTGACTGTA  1560
CATATGTACA  AACACGATAA  AGATGGAAAC  ACATGTAAAA  ACATAAAAAT  AAAAAGTTGT  1620
ACTGGATGTG  GTGGTTTGAA  TGAGATGTTC  CTCGTGTCTC  GGGCATTTGA  AGACTTGCTC  1680
CCCAGTTGTT  GGCGGCTGTT  TGGGAGGCT   TAGAAGATGT  GGCCTTTTGG  GAAGCAGGGT  1740
GTCATTGAGG  ACTGGCTTGG  AGAGCCTAAA  GATCCGAGGC  ACTCCCAGTT  TCTCTGGTTT  1800
TTCATTTTGA  GGTGTGAGGT  CTTATTGGCT  GCACCAGTCT  CCATGCCTGT  CTGTTGCCCG  1860
GCCTCCTCAC  CATGATGGAC  TTTTATCTCT  CTGTACTTGT  AAGCCCAAA   TAAACCTTCC  1920
ATCTGTGAAA  AAAAAAAAA   AAAAAAAA                                       1949
```

( 2 ) INFORMATION FOR SEQ ID NO:4:

(i) SEQUENCE CHARACTERISTICS:
  (A) LENGTH: 432 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:4:

```
Met Val Gly Leu Gln Pro Ser Glu Val Pro Pro Thr Thr Val Val Lys
 1               5                  10                  15
Phe Leu Gly Ala Gly Thr Ala Ala Cys Phe Ala Asp Leu Leu Thr Phe
             20                  25                  30
Pro Leu Asp Thr Ala Lys Val Arg Leu Gln Ile Gln Gly Glu Asn Pro
         35                  40                  45
Gly Ala Gln Ser Val Gln Tyr Arg Gly Val Leu Gly Thr Ile Leu Thr
     50                  55                  60
Met Val Arg Thr Glu Gly Pro Arg Ser Pro Tyr Ser Gly Leu Val Ala
 65                  70                  75                  80
Gly Leu His Arg Gln Met Ser Phe Ala Ser Ile Arg Ile Gly Leu Tyr
                 85                  90                  95
Asp Ser Val Lys Gln Phe Tyr Thr Pro Lys Gly Ala Asp His Ser Ser
            100                 105                 110
Val Ala Ile Arg Ile Leu Ala Gly Cys Thr Thr Gly Ala Met Ala Val
        115                 120                 125
Thr Cys Ala Gln Pro Thr Asp Val Val Lys Val Arg Phe Gln Ala Met
    130                 135                 140
Ile Arg Leu Gly Thr Gly Gly Glu Arg Lys Tyr Arg Gly Thr Met Asp
145                 150                 155                 160
Ala Tyr Arg Thr Ile Ala Arg Glu Glu Gly Val Arg Gly Leu Trp Lys
                165                 170                 175
Gly Thr Trp Pro Asn Ile Thr Arg Asn Ala Ile Val Asn Cys Ala Glu
            180                 185                 190
Met Val Thr Tyr Asp Ile Ile Lys Glu Lys Leu Leu Glu Ser His Leu
        195                 200                 205
Phe Thr Asp Asn Phe Pro Cys His Phe Val Ser Ala Phe Gly Ala Gly
    210                 215                 220
Phe Cys Ala Thr Val Val Ala Ser Pro Val Asp Val Val Lys Thr Arg
225                 230                 235                 240
Tyr Met Asn Ala Pro Leu Gly Arg Tyr Arg Ser Pro Leu His Cys Met
                245                 250                 255
Leu Lys Met Val Ala Gln Glu Gly Pro Thr Ala Phe Tyr Lys Gly Phe
            260                 265                 270
Val Pro Ser Phe Leu Arg Leu Gly Ala Trp Asn Val Met Met Phe Val
        275                 280                 285
Thr Tyr Glu Gln Leu Lys Arg Ala Leu Met Lys Val Gln Gly Val Gly
    290                 295                 300
Lys Ile Glu Ser Glu Ala Asp Met Glu Ala Leu Pro Asn Lys Ala Cys
305                 310                 315                 320
His Arg His His Leu Gln Met Ala Arg Thr Arg Thr Ala Ala Leu Leu
                325                 330                 335
Pro Ser Leu Ser Glu Val Phe Ser Ser Gln Gly Pro Thr Cys Gln Ala
            340                 345                 350
Pro Asp Gln Leu His Leu Pro Thr Leu Pro Pro Ala Leu Ala Ala Phe
        355                 360                 365
```

| | | | | | | | | | | | | |
|---|---|---|---|---|---|---|---|---|---|---|---|---|
|Gly|Cys|Arg|Ala|Phe|Ala|Pro|Pro|Val|Lys|Pro|Ser|Val|Phe|His|Leu|
| |370| | | |375| | | | |380| | | | | |

| | | | | | | | | | | | | |
|---|---|---|---|---|---|---|---|---|---|---|---|---|
|Gln|Lys|Gly|Gly|Gln|Ser|Thr|Gly|Pro|Thr|Ser|Lys|Leu|Lys|Asn|Ala|
|385| | | | |390| | | | |395| | | | |400|

| | | | | | | | | | | | | |
|---|---|---|---|---|---|---|---|---|---|---|---|---|
|His|Leu|Thr|Thr|Lys|Trp|Leu|Ser|Gly|Val|His|Ser|Trp|Asp|Pro|His|
| | | | |405| | | | |410| | | | |415| |

| | | | | | | | | | | | | |
|---|---|---|---|---|---|---|---|---|---|---|---|---|
|Gly|Gly|Arg|Thr|Glu|Trp|Thr|Leu|Ala|Asn|Cys|Pro|Leu|Thr|Ser|Ile|
| | | |420| | | | |425| | | | |430| | |

( 2 ) INFORMATION FOR SEQ ID NO:5:

( i ) SEQUENCE CHARACTERISTICS:
        ( A ) LENGTH: 1777 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:5:

```
GTCAGCTGGT GCACAGGGCC AGTGCCGAGC CAGGGACAGC AGAGACAACA GTGAATGGTG        60
AGGCCCGGCC GTCAGATCCT GCTGCTACCT AATGGAGTGG AGCCTTAGGG TGGCCCTGCA       120
CTACCCAACC TTGGCTAGAC GCACAGCTTC CTCCCTGAAC TGAAGCAAAA GATTGCCAGG       180
CAAGCTCTCT CCTCGGACCT CCATAGGCAG CAAAGGAACC AGGCCCATTC CCCGGGACCA       240
TGGTTGGACT TCAGCCCTCC GAAGTGCCTC CCACAACGGT TGTGAAGTTC CTGGGGGCCG       300
GCACTGCGGC CTGTTTTGCG GACCTCCTCA CTTTTCCCCT GGACACCGCC AAGGTCCGTC       360
TGCAGATCCA AGGGGAGAAC CCAGGGGCTC AGAGCGTGCA GTACCGCGGT GTGCTGGGTA       420
CCATCCTGAC TATGGTGCGC ACAGAGGGTC CCCGCAGCCC CTACAGCGGA CTGGTCGCTG       480
GCCTGCACCG CCAGATGAGT TTTGCCTCCA TTCGAATTGG CCTCTACGAC TCTGTCAAGC       540
AGTTCTACAC CCCCAAGGGA GCGGACCACT CCAGCGTCGC CATCAGGATT CTGGCAGGCT       600
GCACGACAGG AGCCATGGCA GTGACCTGCG CCCAGCCCAC GGATGTGGTG AAGGTCCGAT       660
TTCAAGCCAT GATACGCCTG GGAACTGGAG GAGAGAGGAA ATACAGAGGG ACTATGGATG       720
CCTACAGAAC CATCGCCAGG GAGGAAGGAG TCAGGGGCCT GTGGAAGGGG ACTTGGCCCA       780
ACATCACAAG AAATGCCATT GTCAACTGTG CTGAGATGGT GACCTACGAC ATCATCAAGG       840
AGAAGTTGCT GGAGTCTCAC CTGTTTACTG ACAACTTCCC CTGTCACTTT GTCTCTGCCT       900
TTGGAGCTGG CTTCTGTGCC ACAGTGGTGG CCTCCCCGGT GGATGTGGTA AAGACCCGAT       960
ACATGAACGC TCCCCTAGGC AGGTACCGCA GCAGGACTCA GAATCTTTAG GGAATTGTTA      1020
GGACTGGTAA AAGAATTTCC ACCTTAGGGC AAGAACGAGA ACAGCTGCTC TTCTGCCTTC      1080
TCTCTCGGAG GTTTTCTCAT CTCAGGGTCC TACCTGCCAG GCTCCTGACC AGCTCCACCT      1140
GCCCACACTT CCTCCTGCTC TCGCTGCCTT TGGCTGCAGA GCCTTTGCTC CTCCTGTTAA      1200
GCCTTCAGTC TTCCATCTGC AAAAGGGAGG GCAAAGCACA GGACCAACTT CCAAGCTTAA      1260
AAATGCACAT CTGACAACAA AATGGCTCAG TGGGGTCCAT TCATGGGACC CACATGGTGG      1320
AAGGACAGAA TGGACTCTTG CAAATTGTCC TCTGACCTCC ATTTGAGCGC CCTATACATG      1380
TGACTGTACA TATGTACAAA CACGATAAAG ATGGAAACAC ATGTAAAAAC ATAAAATAA       1440
AAAGTTGTAC TGGATGTGGT GGTTTGAATG AGATGTTCCT CGTGTCTCGG GCATTTGAAG      1500
ACTTGCTCCC CAGTTGTTGG CGGCTGTTTG GGGAGGCTTA GAAGATGTGG CCTTTTGGGA      1560
AGCAGGGTGT CATTGAGGAC TGGCTTGGAG AGCCTAAAGA TCCGAGGCAC TCCCAGTTTC      1620
TCTGGTTTTT CATTTTGAGG TGTGAGGTCT TATTGGCTGC ACCAGTCTCC ATGCCTGTCT      1680
```

-continued

```
GTTGCCCGGC  CTCCTCACCA  TGATGGACTT  TTATCTCTCT  GTACTTGTAA  GCCCCAAATA    1740

AACCTTCCAT  CTGTGAAAAA  AAAAAAAAA   AAAAAA                                1777
```

(2) INFORMATION FOR SEQ ID NO:6:

(i) SEQUENCE CHARACTERISTICS:
        (A) LENGTH: 256 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Met  Val  Gly  Leu  Gln  Pro  Ser  Glu  Val  Pro  Pro  Thr  Thr  Val  Val  Lys
 1              5                        10                       15

Phe  Leu  Gly  Ala  Gly  Thr  Ala  Ala  Cys  Phe  Ala  Asp  Leu  Leu  Thr  Phe
              20                       25                       30

Pro  Leu  Asp  Thr  Ala  Lys  Val  Arg  Leu  Gln  Ile  Gln  Gly  Glu  Asn  Pro
         35                       40                       45

Gly  Ala  Gln  Ser  Val  Gln  Tyr  Arg  Gly  Val  Leu  Gly  Thr  Ile  Leu  Thr
     50                       55                       60

Met  Val  Arg  Thr  Glu  Gly  Pro  Arg  Ser  Pro  Tyr  Ser  Gly  Leu  Val  Ala
65                       70                       75                       80

Gly  Leu  His  Arg  Gln  Met  Ser  Phe  Ala  Ser  Ile  Arg  Ile  Gly  Leu  Tyr
                    85                       90                       95

Asp  Ser  Val  Lys  Gln  Phe  Tyr  Thr  Pro  Lys  Gly  Ala  Asp  His  Ser  Ser
               100                      105                      110

Val  Ala  Ile  Arg  Ile  Leu  Ala  Gly  Cys  Thr  Thr  Gly  Ala  Met  Ala  Val
          115                      120                      125

Thr  Cys  Ala  Gln  Pro  Thr  Asp  Val  Val  Lys  Val  Arg  Phe  Gln  Ala  Met
     130                      135                      140

Ile  Arg  Leu  Gly  Thr  Gly  Gly  Glu  Arg  Lys  Tyr  Arg  Gly  Thr  Met  Asp
145                      150                      155                      160

Ala  Tyr  Arg  Thr  Ile  Ala  Arg  Glu  Glu  Gly  Val  Arg  Gly  Leu  Trp  Lys
                    165                      170                      175

Gly  Thr  Trp  Pro  Asn  Ile  Thr  Arg  Asn  Ala  Ile  Val  Asn  Cys  Ala  Glu
               180                      185                      190

Met  Val  Thr  Tyr  Asp  Ile  Ile  Lys  Glu  Lys  Leu  Leu  Glu  Ser  His  Leu
          195                      200                      205

Phe  Thr  Asp  Asn  Phe  Pro  Cys  His  Phe  Val  Ser  Ala  Phe  Gly  Ala  Gly
     210                      215                      220

Phe  Cys  Ala  Thr  Val  Val  Ala  Ser  Pro  Val  Asp  Val  Val  Lys  Thr  Arg
225                      230                      235                      240

Tyr  Met  Asn  Ala  Pro  Leu  Gly  Arg  Tyr  Arg  Ser  Arg  Thr  Gln  Asn  Leu
                    245                      250                      255
```

NUCLEIC ACIDS ENCODING MURINE UCP3 GENES

INTRODUCTION

1. Field of the Invention

The field of this invention is UCP3 genes and their use in biotechnology.

2. Background

A mitochondrial protein called uncoupling protein (UCP1) is thought to play an important role in the body's regulation of energy utilization. Such regulation provides wide spread physiological controls including body weight, appetite, glucose metabolism, temperature, immune responses, etc. Mechanistically, UCP1 is thought to create a pathway that allows dissipation of the proton electrochemical gradient across the inner mitochondrial membrane in brown adipose tissue, without coupling to any other energy consuming process (for review, see Nicholis & Locke (1984) Physiol Rev 64, 1–64). Unfortunately, the role of UCP1 in physiologies such as body weight regulation in large adult mammals such as people, cattle, pigs, etc. is likely to be limited, since there is little brown adipose tissue in such animals.

UCP2 is a second, related uncoupling protein that is much more widely expressed in large adult mammals (see, e.g. Fleury et al. (1997) Nature Genetics 15, 269–272 and Tartaglia et al. (1996) WO96/05861). Consistent with a role in the regulation of energy utilization generally, and in diabetes and obesity in particular, the UCP2 gene is upregulated in response to fat feeding and maps to regions of the human and mouse genomes linked to hyperinsulinaemia and obesity. More recently, a third structurally related UCP gene, hUCP3 has been charaterized and found to be preferentially expressed in skeletal muscle and brown adipose tissues; see, Vidal-Puig et al. (1997) BBRC 235, 79–82 and Boss et al. (1997) FEBS Letters 408, 39–42.

SUMMARY OF THE INVENTION

The invention provides methods and compositions relating to isolated mUCP3 polypeptides, related nucleic acids, polypeptide domains thereof having mUCP3-specific structure and activity and modulators of mUCP3 function. mUCP3 polypeptides and modulators of mUCP3 expression and/or function can regulate mitochodrial respiration and hence provide important regulators of cell metabolism and function. The polypeptides may be produced recombinantly from transformed host cells or extract from the subject mUCP3 polypeptide encoding nucleic acids or purified from mammalian cells. The invention provides isolated mUCP3 hybridization probes and primers capable of specifically hybridizing with the disclosed mUCP3 genes, mUCP3-specific binding agents such as specific antibodies, and methods of making and using the subject compositions in diagnosis (e.g. genetic hybridization screens for mUCP3 transcripts) and in the biopharmaceutical industry (e.g. as immunogens, reagents for isolating other transcriptional regulators, knockin/out vectors, transgenic animals and cell lines, reagents for screening chemical libraries for lead pharmacological agents, etc.).

BRIEF DESCRIPTION OF THE FIGURES

FIG. 1 shows the amino acid sequence of mUCP3a (SEQ ID NO: 2), indicating the amino acid domains in common with hUCP3 in bold.

FIGS. 2a–2d show the nucleic acid sequence of mUCP3a (SEQ ID NO: 1), indicating the nucleotide domains in common with hUCP3 in bold.

DETAILED DESCRIPTION OF THE INVENTION

Figure 3:
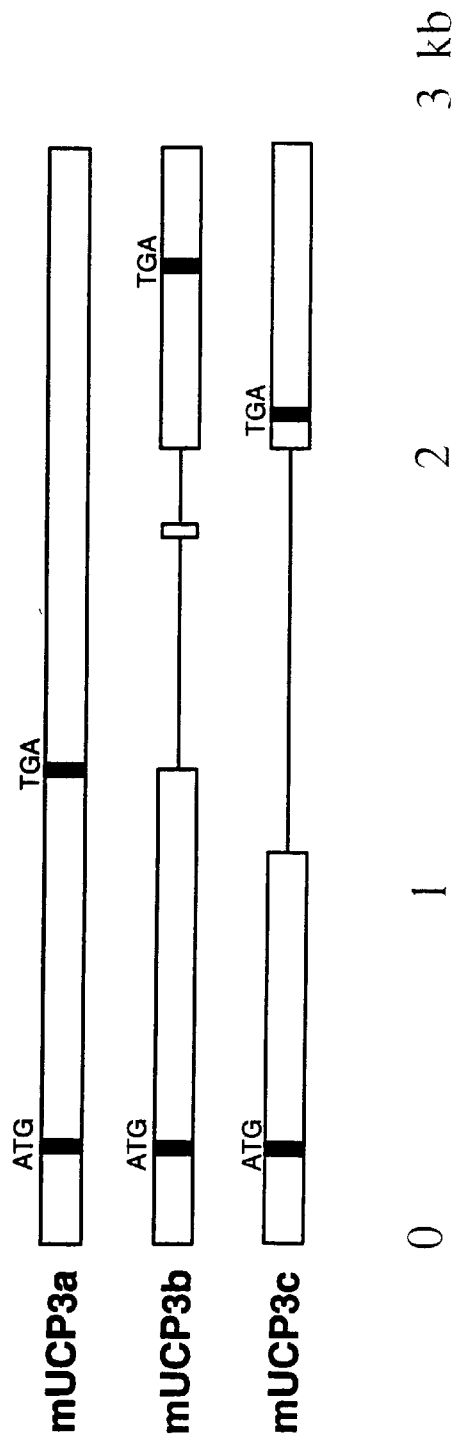
FIG. 3 shows the structures of mUCP3 isoforms a, b and c.

Exemplary nucleotide sequences of natural cDNAs encoding mUCP3 polypeptides are shown as SEQ ID NO: 1, 3 and 5, and their full conceptual translates are shown as SEQ ID NOS: 2, 4 and 6, respectively. The mUCP3 polypeptides of the invention include incomplete translates of SEQ ID NOS: 1, 3 and 5 which translates and deletion mutants of SEQ ID NOS: 2, 4 and 6 have mUCP3-specific amino acid sequence, binding specificity or function. Preferred translates/deletion mutants comprise at least a 6, preferably at least an 8, more preferably at least a 10, most preferably at least a 12 residue domain of the translates not found in hUCP3. Such domains are readily discemable from alignments of mUCP3 polypeptides and hUCP3. See FIG. 1 for the mUCP3a amino acid domains in common (bold) and not in common with hUCP3 and FIGS. 2a–2d for the mUCP3a nucleic acid domains in common (bold) and not in common with the nucleic acid domains of hUCP3.

The subject domains provide mUCP3 domain specific activity or function which are conveniently determined in vitro, cell-based, or in vivo assays: e.g. in vitro binding assays, cell culture assays, in animals (e.g. gene therapy, transgenics, etc.), etc. mUCP3-binding specificity may assayed by binding equilibrium constants (usually at least about $10^7 M^{-1}$, preferably at least about $10^8 M^{-1}$, more preferably at least about $10^9 M^{-1}$), by the ability of the subject polypeptide to function as negative mutants in mUCP3-expressing cells, to elicit mUCP3 specific antibody in a heterologous host (e.g. a rabbit), etc. In any event, the mUCP3 binding specificity of the subject mUCP3 polypeptides necessarily distinguishes that of hUCP3. Preferred peptides demonstrate mUCP3 domain specific activity as assayed by respiratory uncoupling activity, ATP-binding or binding inhibitory activity, mUCP3-specific antibody binding, etc. For example, mUCP3 domain peptides with assay demonstrable mUCP3 domain-specific activities include: SEQ ID NO: 2, residues 3–12; SEQ ID NO: 2, residues 37–58; SEQ ID NO: 2, residues 100–115; SEQ ID NO: 2, residues 144–158; SEQ ID NO: 2, residues 182–198; SEQ ID NO: 2, residues 198–209 SEQ ID NO: 2, residues 242–266; SEQ ID NO: 2, residues 268–290; and SEQ ID NO: 2, residues 297–308.

The subject mUCP3 polypeptides are isolated or pure: an "isolated" polypeptide is unaccompanied by at least some of the material with which it is associated in its natural state, preferably constituting at least about 0.5%, and more preferably at least about 5% by weight of the total polypeptide in a given sample and a pure polypeptide constitutes at least about 90%, and preferably at least about 99% by weight of the total polypeptide in a given sample. A polypeptide, as used herein, is an polymer of amino acids, generally at least 6 residues, preferably at least about 10 residues, more preferably at least about 25 residues, most preferably at least about 50 residues in length. The mUCP3 polypeptides and polypeptide domains may be synthesized, produced by recombinant technology, or purified from mammalian, preferably murine cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art. For example, the invention provides a method of making a polypeptide comprising the steps of introducing an isolated or recombinant nucleic acid encoding an mUCP3 polypeptide into a host cell or extract, incubating said host cell or extract under conditions whereby said isolated or recombinant nucleic acid is expressed as a transcript and said transcript is expressed as a translation product comprising said polypeptide, and isolating said translation product.

The invention provides binding agents specific to the claimed mUCP3 polypeptides, including substrates, agonists, antagonists, natural intracellular binding targets, etc., methods of identifying and making such agents, and their use in pharmaceutical development. Novel mUCP3-specific binding agents include mUCP3-specific receptors, such as somatically recombined polypeptide receptors like specific antibodies or T-cell antigen receptors (see, e.g. Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as described below, etc. Agents of particular interest modulate mUCP3 function, e.g. mUCP3-dependent respiratory coupling.

Accordingly, the invention provides methods for modulating respiration involving an mUCP3 gene product comprising the step of modulating mUCP3 activity, e.g. by contacting the cell with an mUCP3-specific binding agent. The cell may reside in culture or in situ, i.e. within the natural host. Preferred inhibitors are orally active in mammalian hosts. For diagnostic uses, the inhibitors or other mUCP3 binding agents are frequently labeled, such as with fluorescent, radioactive, chemiluminescent, or other easily detectable molecules, either conjugated directly to the binding agent or conjugated to a probe specific for the binding agent.

The amino acid sequences of the disclosed mUCP3 polypeptides are used to back-translate mUCP3 polypeptide-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural mUCP3-encoding nucleic acid sequences ("GCG" software, Genetics Computer Group, Inc, Madison Wis.). mUCP3-encoding nucleic acids used in mUCP3-expression vectors and incorporated into recombinant host cells, e.g. for expression and screening, transgenic animals, e.g. for functional studies such as the efficacy of candidate drugs for disease associated with mUCP3-modulated cell function, etc.

The invention also provides nucleic acid hybridization probes, knockin/out constructs and replication/amplification primers having a mUCP3 cDNA specific sequence comprising SEQ ID NOS: 1, 3 and 5, or fragments thereof sufficient to effect specific hybridization thereto (i.e. specifically hybridize with SEQ ID NOS: 1, 3 and 5 in the presence of the UCP1, UCP2 and hUCP3 cDNA. Such primers or probes are at least 12, preferably at least 24, more preferably at least 36 and most preferably at least 96 bases in length. Demonstrating specific hybridization generally requires stringent conditions, for example, hybridizing in a buffer comprising 30% formamide in 5×SSPE (0.18M NaCl, 0.01M NaPO$_4$, pH7.7, 0.001M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. mUCP3 nucleic acids can also be distinguished using alignment algorithms, such as BLASTX (Altschul et al. (1990) Basic Local Alignment Search Tool, J Mol Biol 215, 403–410).

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Recombinant nucleic acids comprising the nucleotide sequence of SEQ ID NOS: 1, 3 and 5, or fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, knockin/out constructsetc.; use in detecting the presence of mUCP3 genes and gene transcripts and in detecting or amplifying nucleic acids encoding additional mUCP3 homologs and structural analogs. In diagnosis, mUCP3 hybridization probes find use in identifying wild-type and mutant mUCP3 alleles in clinical and laboratory samples. In a particular embodiment, mUCP3 nucleic acids are used to modulate cellular expression or intracellular concentration or availability of active mUCP3 by binding and/or recombining with an endogenous mUCP3 gene or gene transcript. Methods for effecting anti-sense hyridization, homologous and non-homologous recombinations, and generating transgenic animals and cell lines are well-established in the art.

The following experimental section and examples are offered by way of illustration and not by way of limitation.

EXAMPLES

1. Cloning of mUCP3 cDNAs

We searched murine EST databases using human UCP2 cDNA sequence to identify a CDNA with sequence similarity to known human and mouse UCP2 cDNA sequences. Isolated, cloning and sequencing of this clone revealed a novel gene designated mUCP3, with greatest sequence similarity to a human UCP3 gene. Since the clone lacked the 5' end UTR and part of the coding sequence, we designed a primer for 5' end RACE of the cDNA sequence using mouse skeletal muscle cDNA (PCR condition: 95 0C, 40 sec, 55 0C 2 min, 72 0C, 3 min for 30 cycles). Several clones from the RACE PCR contain sequences that overlap with the partial cDNA sequence. A EcoRI tagged forward primer and XbaI tagged reverse primer were used to amplify the fall mUCP3 cDNA using mouse skeletal muscle cDNA. A 2.8 kb mUCP3 cDNA was amplified and cloned into pBlue-Script SK. Several smaller fragments (1.5–2 kb) detected in the PCR products in lesser quantities were also cloned and DNA sequencing confirmed that they were alternatively spliced forms of mUCP3 cDNA.

The largest mUCP3 cDNA (mUCP3a) is 2,782 bp long, containing 239 bp 5' end untranslated region, a 816 bp ORF and 1.7 kb 3' end UTR. The mRNA transcript is about 2.8 kb and the translation product contains 308 amino acid residues. It is 85% identical to the hUCP3 and 73% and 54% identical to mUCP2 and mUCP1, respectively, indicating a similar functional roles in uncoupling mitochondrial respiration. Two shorter isoforms, mUCP3b and mUCP3c are 1,949 bp and 1,777 bp, with translation products of 432 and 256 amino acid residues respectively (see, FIG. 3).

2. Expression of mUCP3 cDNAs

Because of the extensive DNA sequence homology between our mUCP3 genes and mUCP2, we designed a set of primers designed for PCR amplification of a 335 bp mUCP3 specific DNA sequence and cloned into pBlueScript SK. The cloned fragment was labeled through reverse transcription using a T3/T7 Reverse Transcription Kit from Ambion and used as a probe for Northern blot analysis of mUCP3 expression. The mouse multiple tissue blots were purchased from Clontech and Northern analysis was performed using a Northern Max kit purchased from Ambion. Northern analysis revealed specific enhanced expression in heart and especially skeletal muscle tissues as compared with negligble expression in brain, spleen, lung, liver, kidney and testis tissues.

3. Protocol for high throughput mUCP3a—antibody binding assay.

A. Reagents:

Neutralite Avidin: 20 $\mu$g/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM MgCl$_2$, 1% glycerol, 0.5% NP-40, 50 mM β-mercaptoethanol, 1 mg/ml BSA, cocktail of protease inhibitors.

$^{33}$P mUCP3a polypeptide 10x stock: $10^{-8}$–$10^{-6}$M "cold" mUCP3 supplemented with 200,000–250,000 cpm of labeled mUCP3a (Beckman counter). Place in the 4° C. microfridge during screening.

Protease inhibitor cocktail (1000X): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVO$_3$ (Sigma #S-6508) in 10 ml of PBS.

mUCP3-specific antibody: $10^{-7}$–$10^{-5}$M biotinylated antibody in PBS.

B. Preparation of assay plates:

Coat with 120 $\mu$l of stock N-Avidin per well overnight at 4° C.

Wash 2 times with 200 $\mu$l PBS.

Block with 150 $\mu$l of blocking buffer. p1 Wash 2 times with 200 $\mu$l PBS.

C. Assay:

Add 40 $\mu$l assay buffer/well.

Add 10 $\mu$l compound or extract.

Add 10 $\mu$l $^{33}$P-mUCP3a (20–25,000 cpm/0.1–10 pmoles/well=$10^{-9}$–$10^{-7}$M final conc).

Shake at 25° C. for 15 minutes.

Incubate additional 45 minutes at 25° C.

Add 40 $\mu$M biotinylated antibody (0.1–10 pmoles/40 ul in assay buffer)

Incubate 1 hour at room temperature.

Stop the reaction by washing 4 times with 200 $\mu$M PBS.

Add 150 $\mu$M scintillation cocktail.

Count in Topcount.

D. Controls for all assays (located on each plate):

a. Non-specific binding b. Soluble (non-biotinylated antibody) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated or recombinant nucleic acid encoding a polypeptide comprising the amino acid sequence set forth as SEQ ID NO: 2, 4 or 6.

2. The isolated or recombinant nucleic acid according to claim 1, wherein the isolated or recombinant nucleic acid encodes a polypeptide comprising the amino acid sequence set forth as SEQ ID NO: 2.

3. A cell comprising the recombinant nucleic acid according to claim 2.

4. A method of making a polypeptide, said method comprising the steps of:

a) introducing the isolated or recombinant nucleic acid according to claim 2 into a host cell or extract;

b) incubating said host cell or extract under conditions whereby said isolated or recombinant nucleic acid is expressed as a transcript and said transcript is expressed as a translation product comprising said polypeptide; and c) isolating said translation product.

5. The isolated or recombinant nucleic acid according to claim 1, wherein the isolated or recombinant nucleic acid encodes a polypeptide comprising the amino acid sequence set forth as SEQ ID NO: 4.

6. A cell comprising the recombinant nucleic acid according to claim 5.

7. A method of making a polypeptide, said method comprising the steps of:
   a) introducing the isolated or recombinant nucleic acid according to claim 5 into a host cell or extract;
   b) incubating said host cell or extract under conditions whereby said isolated or recombinant nucleic acid is expressed as a transcript and said transcript is expressed as a translation product comprising said polypeptide; and
   c) isolating said translation product.

8. The isolated or recombinant nucleic acid according to claim 1, wherein the isolated or recombinant nucleic acid encodes a polypeptide comprising the amino acid sequence set forth as SEQ ID NO: 6.

9. A cell comprising the recombinant nucleic acid according to claim 8.

10. A method of making a polypeptide, said method comprising the steps of:
    a) introducing the isolated or recombinant nucleic acid according to claim 8 into a host cell or extract;
    b) incubating said host cell or extract under conditions whereby said isolated or recombinant nucleic acid is expressed as a transcript and said transcript is expressed as a translation product comprising said polypeptide; and
    c) isolating said translation product.

11. An isolated or recombinant nucleic acid comprising an entire strand of the nucleic acid sequence set forth as SEQ ID NO: 1, 3 or 5.

12. The isolated or recombinant nucleic acid according to claim 11, wherein the isolated or recombinant nucleic acid comprises an entire strand of the nucleic acid sequence set forth as SEQ ID NO: 1.

13. A cell comprising the recombinant nucleic acid according to claim 12.

14. A method of making a polypeptide, said method comprising the steps of:
    a) introducing the isolated or recombinant nucleic acid according to claim 12 into a host cell or extract;
    b) incubating said host cell or extract under conditions whereby said isolated or recombinant nucleic acid is expressed as a transcript and said transcript is expressed as a translation product comprising said polypeptide; and
    c) isolating said translation product.

15. The isolated or recombinant nucleic acid according to claim 11, wherein the isolated or recombinant nucleic acid comprises an entire strand of the nucleic acid sequence set forth as SEQ ID NO: 3.

16. A cell comprising the recombinant nucleic acid according to claim 15.

17. A method of making a polypeptide, said method comprising the steps of:
    a) introducing the isolated or recombinant nucleic acid according to claim 15 into a host cell or extract;
    b) incubating said host cell or extract under conditions whereby said isolated or recombinant nucleic acid is expressed as a transcript and said transcript is expressed as a translation product comprising said polypeptide; and
    c) isolating said translation product.

18. The isolated or recombinant nucleic acid according to claim 11, wherein the isolated or recombinant nucleic acid comprises an entire strand of the nucleic acid sequence set forth as SEQ ID NO: 5.

19. A cell comprising the recombinant nucleic acid according to claim 18.

20. A method of making a polypeptide, said method comprising the steps of:
    a) introducing the isolated or recombinant nucleic acid according to claim 18 into a host cell or extract;
    b) incubating said host cell or extract under conditions whereby said isolated or recombinant nucleic acid is expressed as a transcript and said transcript is expressed as a translation product comprising said polypeptide; and
    c) isolating said translation product.

* * * * *